US008790265B2

(12) United States Patent
Mohl et al.

(10) Patent No.: US 8,790,265 B2
(45) Date of Patent: *Jul. 29, 2014

(54) METHOD AND DEVICE FOR THE INTERMITTENT OCCLUSION OF THE CORONARY SINUS

(75) Inventors: Werner Mohl, Altenmarkt-Thennenberg (AT); Loay Alzubaidi, Bahrain-Saar (AT)

(73) Assignee: Miracor Medical Systems GmbH, Vienna (AT)

( * ) Notice: Subject to any disclaimer, the term of this patent is extended or adjusted under 35 U.S.C. 154(b) by 43 days.

This patent is subject to a terminal disclaimer.

(21) Appl. No.: 13/593,984

(22) Filed: Aug. 24, 2012

(65) Prior Publication Data

US 2012/0323065 A1    Dec. 20, 2012

Related U.S. Application Data

(63) Continuation of application No. 12/855,473, filed on Aug. 12, 2010, now Pat. No. 8,262,580, which is a continuation of application No. 11/597,834, filed as application No. PCT/AT2005/000204 on Jun. 7, 2005, now Pat. No. 7,780,604.

(30) Foreign Application Priority Data

Jun. 8, 2004   (AT) .................................... A9932004

(51) Int. Cl.
*A61B 5/02*   (2006.01)
(52) U.S. Cl.
USPC ............... 600/485; 600/480; 600/16; 600/17; 600/18

(58) Field of Classification Search
USPC .............................. 600/16–18, 485, 486, 480
See application file for complete search history.

(56) References Cited

U.S. PATENT DOCUMENTS

| 1,611,914 A | 12/1926 | Jenkins |
| 3,995,623 A | 12/1976 | Blake et al. |
| 4,589,869 A | 5/1986 | Wernborg |

(Continued)

FOREIGN PATENT DOCUMENTS

| EP | 0 230 996 | 8/1987 |
| EP | 1 611 914 | 1/2006 |

(Continued)

OTHER PUBLICATIONS

'Cannulation' [online] Medtronic, Inc. 2010 [retrieved May 27, 2010]. Retrieved from the Internet: <URL: http://www.medtronic.com/for-healthcare-professionals/products-therapies/cardiovascular/therapies/cannulation/index.htm>.

(Continued)

*Primary Examiner* — Michael D'Angelo
(74) *Attorney, Agent, or Firm* — Fish & Richardson P.C.

(57) ABSTRACT

In a method for intermittently occluding the coronary sinus, in which the coronary sinus is occluded using an occlusion device, the fluid pressure in the occluded coronary sinus is continuously measured and stored, the fluid pressure curve is determined as a function of time, and the occlusion of the coronary sinus is triggered and/or released as a function of at least one characteristic value derived from the measured pressure values. The pressure increase and/or pressure decrease per time unit each occurring at a heart beat are used as characteristic values.

10 Claims, 4 Drawing Sheets

(56) References Cited

U.S. PATENT DOCUMENTS

| | | | |
|---|---|---|---|
| 4,657,536 | A | 4/1987 | Dorman |
| 4,670,009 | A | 6/1987 | Bullock |
| 4,671,796 | A | 6/1987 | Groshong et al. |
| 4,701,166 | A | 10/1987 | Groshong et al. |
| 4,705,501 | A | 11/1987 | Wigness et al. |
| 4,887,608 | A | 12/1989 | Mohl et al. |
| 4,931,036 | A | 6/1990 | Kanai et al. |
| 4,934,996 | A * | 6/1990 | Mohl et al. ............ 600/17 |
| 4,943,277 | A | 7/1990 | Bolling |
| 4,969,470 | A | 11/1990 | Mohl et al. |
| 5,021,045 | A | 6/1991 | Buckberg et al. |
| 5,024,668 | A | 6/1991 | Peters et al. |
| 5,156,600 | A | 10/1992 | Young |
| 5,224,938 | A | 7/1993 | Fenton, Jr. |
| 5,226,427 | A | 7/1993 | Buckberg et al. |
| 5,324,260 | A | 6/1994 | O'Neill et al. |
| 5,456,665 | A | 10/1995 | Postell et al. |
| 5,458,574 | A | 10/1995 | Machold et al. |
| 5,466,216 | A | 11/1995 | Brown et al. |
| 5,505,698 | A | 4/1996 | Booth et al. |
| 5,683,347 | A | 11/1997 | Miyata et al. |
| 5,707,358 | A | 1/1998 | Wright |
| 5,755,686 | A | 5/1998 | O'Neill et al. |
| 5,775,327 | A | 7/1998 | Randolph et al. |
| 5,779,685 | A | 7/1998 | Thompson et al. |
| 6,029,671 | A | 2/2000 | Stevens et al. |
| 6,179,856 | B1 | 1/2001 | Barbere |
| 6,475,209 | B1 | 11/2002 | Larson et al. |
| 6,500,145 | B1 | 12/2002 | Bicakci et al. |
| 6,506,146 | B1 | 1/2003 | Mohl et al. |
| 6,508,777 | B1 | 1/2003 | Macoviak et al. |
| 6,569,145 | B1 | 5/2003 | Shmulewitz et al. |
| 6,673,040 | B1 | 1/2004 | Samson et al. |
| 6,758,854 | B1 | 7/2004 | Butler et al. |
| 7,166,100 | B2 | 1/2007 | Jordan et al. |
| 7,331,922 | B2 | 2/2008 | Mohl et al. |
| 7,780,604 | B2 | 8/2010 | Mohl et al. |
| 8,262,580 | B2 | 9/2012 | Mohl et al. |
| 2001/0053920 | A1 | 12/2001 | Shaker |
| 2002/0072730 | A1 | 6/2002 | McGill et al. |
| 2002/0120232 | A1 | 8/2002 | Stumpp et al. |
| 2003/0032974 | A1 | 2/2003 | Leschinsky et al. |
| 2004/0172004 | A1 | 9/2004 | Mohl |
| 2005/0015048 | A1 | 1/2005 | Chiu et al. |
| 2006/0074399 | A1 | 4/2006 | Bates |
| 2007/0083126 | A1 | 4/2007 | Marko et al. |
| 2008/0015404 | A1 | 1/2008 | Mohl |
| 2008/0119742 | A1 | 5/2008 | Mohl |
| 2010/0056849 | A1 | 3/2010 | Mohl |
| 2010/0130810 | A1 | 5/2010 | Mohl |

FOREIGN PATENT DOCUMENTS

| | | |
|---|---|---|
| UA | 14911 U | 6/2006 |
| WO | WO 89/10155 | 11/1989 |
| WO | 03/008018 | 1/2003 |
| WO | WO 03/008018 | 1/2003 |
| WO | WO 03/041783 | 5/2003 |

OTHER PUBLICATIONS

'Cardioplegia Delivery' [online] Quest Medical, Inc. 2010 [retrieved May 27, 2010]. Retrieved from the Internet: <URL: http://www.questmedical.com/products/cardio_catheters.asp>.

'Global Myocardial Protection' [online] Edwards Lifesciences, 2004 [retrieved May 27, 2010]. Retrieved from the Internet: <URL: http://ht.edwards.com/resourcegallery/products/cannulae/images.ar00519.pdf>.

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010]. Retrieved from the Internet: <URL: http://www.anesthesia-analgesia.org/content/97/1/298.full.pdf>.

'MiRCSP Cannulae' [online]. Medtronic, Inc. 2010 [retrieved May 27, 2010]. Retrieved from the Internet: <URL: http://www.medironic.com/for-healthcare-professionals/products-therapies/cardiovascular/cannulae-products/mircsp-cannula/index.htm>.

'Myocardial Protection System' [online]. Quest Medical, Inc. 2010 [retrieved May 27, 2010]. Retrieved from the Internet: <URL: http://www.questmedical.com/products/mps.asp>.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>.

'Retrograde Perfusion Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/retrograde-perfusion-cannulae/index.htm>.

Mohl, Werner et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Mohl, Werner et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.

International Search Report for PCT/AT2005/000204 mailed Aug. 24, 2005, 6 pages.

Mohl, Werner et al. "Coronary Sinus Library, ICSO and PICSO" Society of Coronary Sinus Interventions, 2003. A. Holzhausens Nfg., Austria.

Mohl et al., "Intermittent pressure elevation of the coronary venous system as a method to protect ischemic myocardium," *Interact CardioVac Thorac Surg.*, 2005, 4:66-69.

Syeda et al., "The salvage potential of coronary sinus interventions: Meta-analysis and pathophysiologic consequences," *J Thorac Cardiovasc Surg.*, 2004, 124:1703-1712.

\* cited by examiner

METHOD AND DEVICE FOR THE INTERMITTENT OCCLUSION OF THE CORONARY SINUS

CROSS-REFERENCE TO RELATED APPLICATIONS

This application is a continuation of U.S. application Ser. No. 12/855,473 filed on Aug. 12, 2010, which is a continuation of U.S. application Ser. No. 11/597,834 filed on Nov. 28, 2006, which is a U.S. national phase of PCT application PCT/AT2005/000204 filed on Jun. 7, 2005, which claims priority to Austrian patent application no. AT A 993/2004 filed on Jun. 8, 2004, the entire contents of each of which are hereby incorporated by reference

TECHNICAL FIELD

The invention relates to a method for intermittently occluding the coronary sinus, in which the coronary sinus is occluded using an occlusion device, the fluid pressure in the occluded coronary sinus is continuously measured and stored, the fluid pressure curve is determined as a function of time, and the occlusion of the coronary sinus is triggered and/or released as a function of at least one characteristic value derived from the measured pressure values, as well as a device for the intermittent occlusion of the coronary sinus.

BACKGROUND

Arterial blood, which supplies the heart muscle, is able to pass through healthy heart tissue while nourishing the same, yet has difficulty reaching ischemic tissue. As a result, the supply of ischemic tissue with nutrients and the discharge of metabolic catabolites from such ischemic tissue will be impaired.

In this context, it has already been proposed to supply ischemic tissue with blood through retrograde perfusion. This means that blood is tried to be allowed to flow back from the coronary sinus through the coronary venous system in counterflow by feeding blood from a different source into the coronary sinus, either by permanently connecting an artery with the coronary sinus or by temporarily inserting a catheter into the sinus, which catheter is supplied with blood taken from a remote artery and transported by the aid of a blood pump located outside the patient's body.

Another technique proposed for retroperfusion uses an inflatable balloon which is fixed to the end of a catheter to intermittently occlude the coronary sinus. The blood pressure in the coronary sinus rises during the occlusion at every heart beat so as to cause blood reaching the coronary sinus through the healthy tissue of the heart muscle to be flushed back into the ischemic tissue. For such an intermittent coronary sinus occlusion, the balloon end of the catheter is inserted either percutaneously or surgically. The other end of the catheter is supplied with a gas or fluid by a pump which causes the cyclic inflation and deflation of the balloon.

A typical application of blood retroinfusion in coronary veins through intermittent coronary sinus occlusion applies to myocardial protection during a short-term coronary arterial occlusion in the context of a cardiologic intervention. A typical such intervention comprises, for instance, the balloon dilatation of an arteriosclerotically constricted coronary artery. That method, which is also known as percutaneous transluminal coronary angioplasty (PTCA), comprises the conduction of a balloon catheter into the region of the coronary artery stenosis under X-ray control and the compression of the osclerotic plaque by the inflation of the balloon, which is located on the end of the catheter. During the dilatation of the balloon, no supply of the tissue with oxygen-containing blood takes place downstream in the artery with functional changes in the ischemic area of the myocard being detectable already at dilatations lasting longer than 30 seconds. Consequential problems of the ischemic protection of the myocard will also be faced with other interventions aimed at coronary vascularization such as, e.g., atherectomy, coronary endoprostheses and laser applications.

A device for the retroinfusion of coronary veins is, for instance, known from U.S. Pat. No. 4,934,996, by which a pressure-controlled, intermittent coronary sinus occlusion can be performed. The device comprises a means for occluding the sinus such as, e.g., an inflatable balloon catheter, a pressure measuring unit for measuring the fluid pressure within the coronary sinus and a control unit which generates triggering signals for the occlusion device to trigger or release an occlusion. The control unit is devised in a manner that the pressure maximum in the coronary sinus is measured during every heart beat, a plateau value of the pressure maxima of consecutive heart beats is estimated by calculation and the occlusion of the coronary sinus is released on the basis of the plateau value of the pressure maxima.

The occlusion of the coronary sinus causes a pressure increase and, as a result, a retroperfusion of blood via the respective vein into the nutritive capillaries of the ischemic area so as to enable the supply of nutrients to that area. At a release of the occlusion, the retroperfused blood is flushed out while the metabolic waste products are carried off at the same time. In the method according to U.S. Pat. No. 4,934,996, a systolic pressure curve is, thus, estimated based on the measurement of the pressure maximum in the coronary sinus during every heart beat, with the intermittent occlusion being controlled as a function of the plateau value of the systolic pressure curve. The course of the estimated systolic pressure curve also allows for a conclusion as to the efficiency of the heart, with the slope of the curve reflecting, for instance, the contractibility of the heart.

Under certain circumstances, the determination of the moment of release of the occlusion by way of plateau values of the systolic pressure curve according to U.S. Pat. No. 4,934,996 is, however, not feasible with sufficient accuracy.

SUMMARY

The present invention, therefore, aims to propose a method and device for the intermittent occlusion of the coronary sinus, in which characteristic values are used to control the occlusion, which permit the determination of the precise time at which the occlusion of the coronary sinus is to be released or triggered. At the same time, it is to be ensured that the time of release, or the time of triggering, of the occlusion is selected with a view to optimizing therapeutic and/or diagnostic effects while preventing an impairment of the heart muscle.

To solve this object, the method according to the invention essentially consists in that the pressure increase and/or pressure decrease per time unit each occurring at a heart beat is used as said characteristic value. The respective device according to the invention includes an occlusion device, a pressure measuring device for continuously measuring the fluid pressure in the occluded coronary sinus, and a memory for storing the fluid pressure curve as a function of time, and is characterized in that an evaluation circuit is provided for the determination of the pressure increase and/or pressure decrease per time unit each occurring at a heart beat, which cooperates with the occlusion device to trigger and/or release the occlusion of the coronary sinus. The pressure increase or pressure decrease per time unit each reflects the positive or negative gradient of the fluid pressure curve to be observed within a heart beat and, departing from the fluid pressure curve, is calculated as a function of time and the pressure increase or pressure decrease ($\Delta p$) readable from this function within a time interval ($\Delta t$) as follows: $(\Delta p)/(\Delta t)$. This characteristic value enables the attending physician to make conclusions as to the contractibility of the heart and the conditions within the coronary sinus both during the occlusion of the coronary sinus (occlusion phase) and also after the release of the occlusion (release phase), in order to deduce therefrom the optimum occlusions times. To this end, it is surprisingly not necessary to know the pressure prevailing within the coronary sinus in absolute numbers, but it will do according to the invention to evaluate pressure differences, i.e. the pressure increase or pressure decrease respectively occurring per time unit within a heart beat.

The pressure curve in the occluded coronary sinus, as a rule, extends in a manner that the speed of the pressure increase rises with every heart beat and, hence, ever increasing systolic pressure peaks will occur until a so-called "plateau phase" will have been reached, in which the speed of the pressure increase will further rise at consecutive heart beats, yet the systolic pressure will already have attained a plateau value, thus remaining substantially constant. It is only when the contractibility of the heart decreases in this plateau phase by arterial underperfusion (coronary resistance increase) that the speed of the pressure increase will drop again, with the systolic pressure substantially continuing to remain on the plateau value. If, as in accordance with the present invention and deviating from the prior art, the determination of the optimum time of release of the occlusion is not based on absolute pressure values such as, for instance, the plateau value of the systolic pressure peaks, but on the speed of the pressure increase, it will be feasible to maintain the occlusion over an extended period of time without affecting the heart. It is, in fact, possible to only release the occlusion at a time at which the speed of the pressure increase during consecutive heart beats has attained a maximum, or at a time at which a predetermined percentage of the calculated or estimated maximum of the speed of the pressure increase has been reached, which time is after the achievement of the systolic plateau value. The fact that the occlusion can be maintained over an extended period of time without overstressing or affecting the heart or heart vessels advantageously results in an augmented release of angiopoietic genes (VEGF genes, vascular endothelial growth factor encoding genes) due to the pressure increase lasting as long as possible, which will also be beneficial to the regeneration of the vessels.

The control of the release or triggering of the occlusion as a function of the pressure increase or pressure decrease, respectively, per time unit may be realized in various ways. The occlusion might, for instance, be released as soon as a predetermined upper limit value for the characteristic value $\Delta p/\Delta t$ has been exceeded or, vice versa, might be triggered as the characteristic value $\Delta p/\Delta t$ is falling short of a lower limit value. According to a preferred method variant, it is, however, proceeded according to the invention in a manner that the pressure increase per time unit occurring at a heart beat is determined and the occlusion of the coronary sinus is released after the pressure increase per time unit of consecutive heart beats has attained a maximum, wherein the respective device in this case is devised such that the evaluation circuit is configured to determine the pressure increase per time unit each occurring at a heart beat, and cooperates with the occlusion device in a manner that the occlusion of the coronary sinus is released after the pressure increase per time unit of consecutive heart beats has reached a maximum. This ensures the precise determination of the optimum length of the occlusion time. For the period of the release phase, it may analogously be proceeded in a manner that the pressure decrease per time unit occurring at a heart beat is determined and the occlusion is triggered after the pressure decrease per time unit of consecutive heart beats has reached a minimum.

A further refinement of the method, which is particularly easy to realize using a mathematical algorithm, is feasible for the occlusion phase in that the first derivative of the fluid pressure is calculated with respect to time, that the local maximum each occurring within a heart beat, of the first derivative is determined, and that the occlusion of the coronary sinus is released after the local maxima of consecutive heart beats have reached a maximum. For the release phase, it is analogously provided in a preferred manner that the first derivative of the fluid pressure is calculated with respect to time, that the local minimum each occurring within a heart beat, of the first derivative is determined, and that the occlusion of the coronary sinus is triggered after the local minima of consecutive heart beats have reached a minimum.

For the implementation of this preferred method, the device according to the invention is advantageously further developed in that the evaluation circuit is configured to determine the first derivative of the fluid pressure with respect to time as well as the local maximum of the first derivative each occurring within a heart beat, and cooperates with the occlusion device in a manner that the occlusion of the coronary sinus is released after the local maxima of consecutive heart beats have reached a maximum. In an analogous manner, a configuration is advantageously provided for the release phase, in which the evaluation circuit is configured to determine the first derivative of the fluid pressure with respect to time as well as the local minimum of the first derivative each occurring within a heart beat, and cooperates with the occlusion device in a manner that the occlusion of the coronary sinus is triggered after the local minima of consecutive heart beats have reached a minimum.

DESCRIPTION OF DRAWINGS

In the following, the invention will be explained in more detail by way of an exemplary embodiment illustrated in the drawings. Therein.

DESCRIPTION

Figure 1:
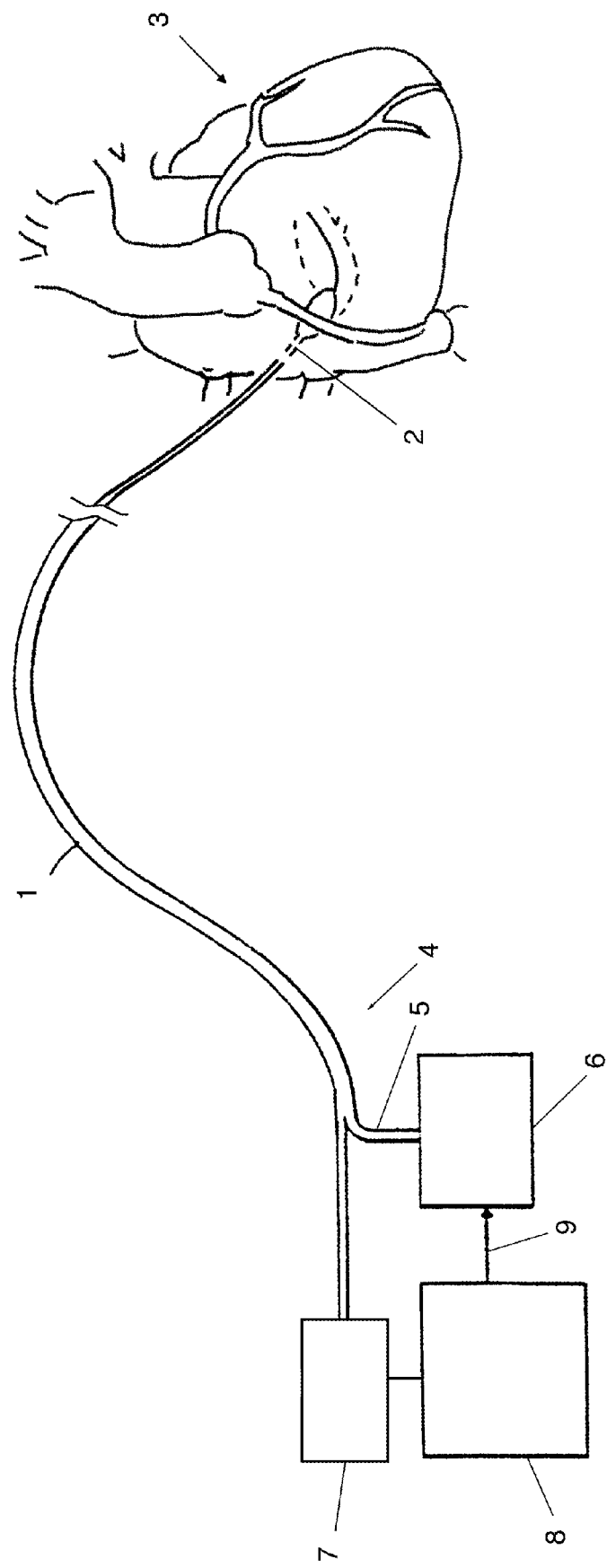
FIG. 1 is a diagrammatic view of a heart including a device for the intermittent occlusion of the coronary sinus.

FIG. 1 schematically depicts the device for the intermittent occlusion of the coronary sinus with a multilumen catheter 1 being apparent, whose distal end 2 is inserted in the coronary sinus of the heart 3 via the atrium. The proximal end 4 of the catheter 1 has a balloon inflation lumen 5 connected with a pump 6. The pressure prevailing on the distal end 2 of the catheter 1 is detected by a pressure measuring device 7, the latter also including a memory for the measured values acquired. The respectively measured pressure values are fed to a control device via an evaluation circuit 8 in order to deliver control signals via line 9 for the start and stop of the pump 6.

Figure 2A:
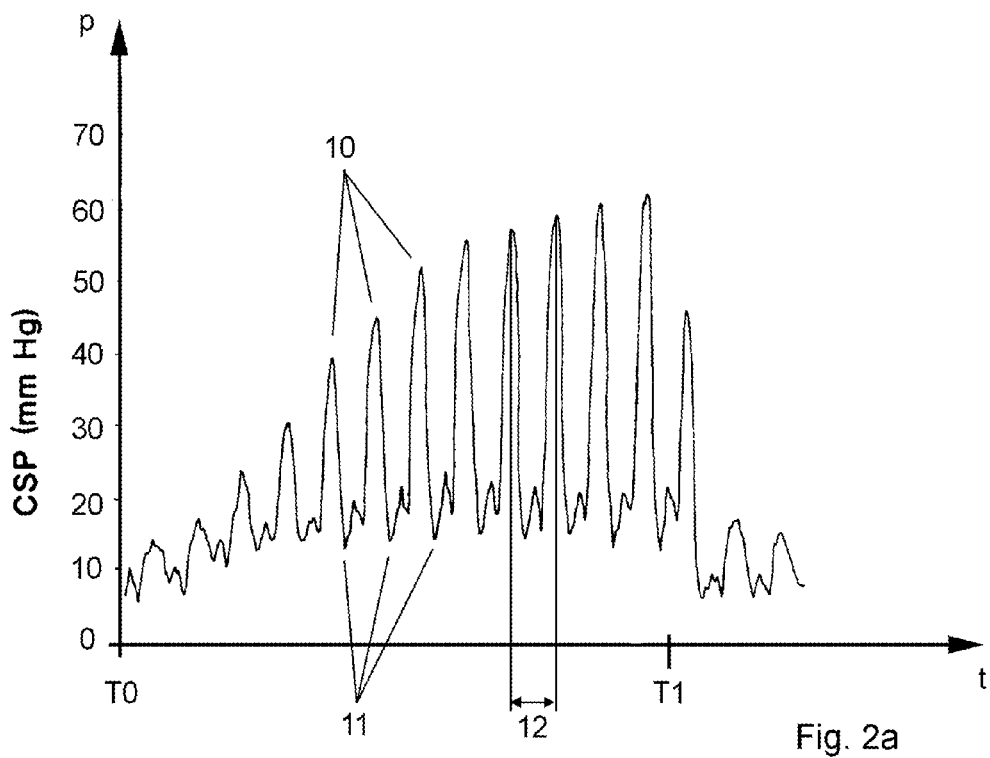
FIG. 2 is a graphical representation of the coronary sinus pressure curve.
Figure 2B:
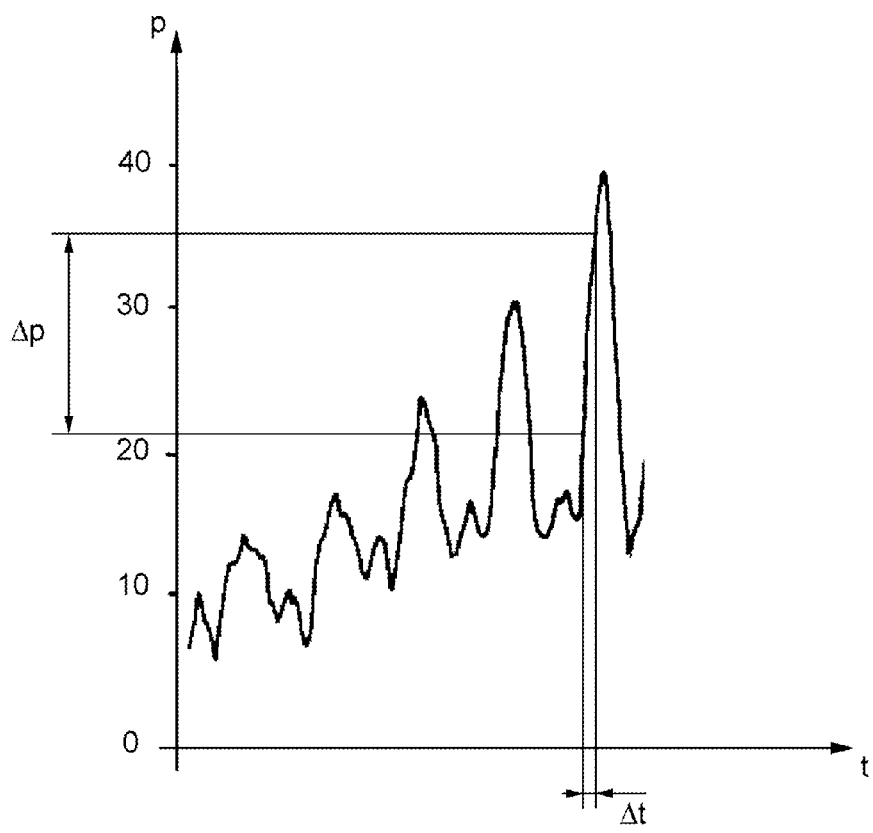
Figure 3:
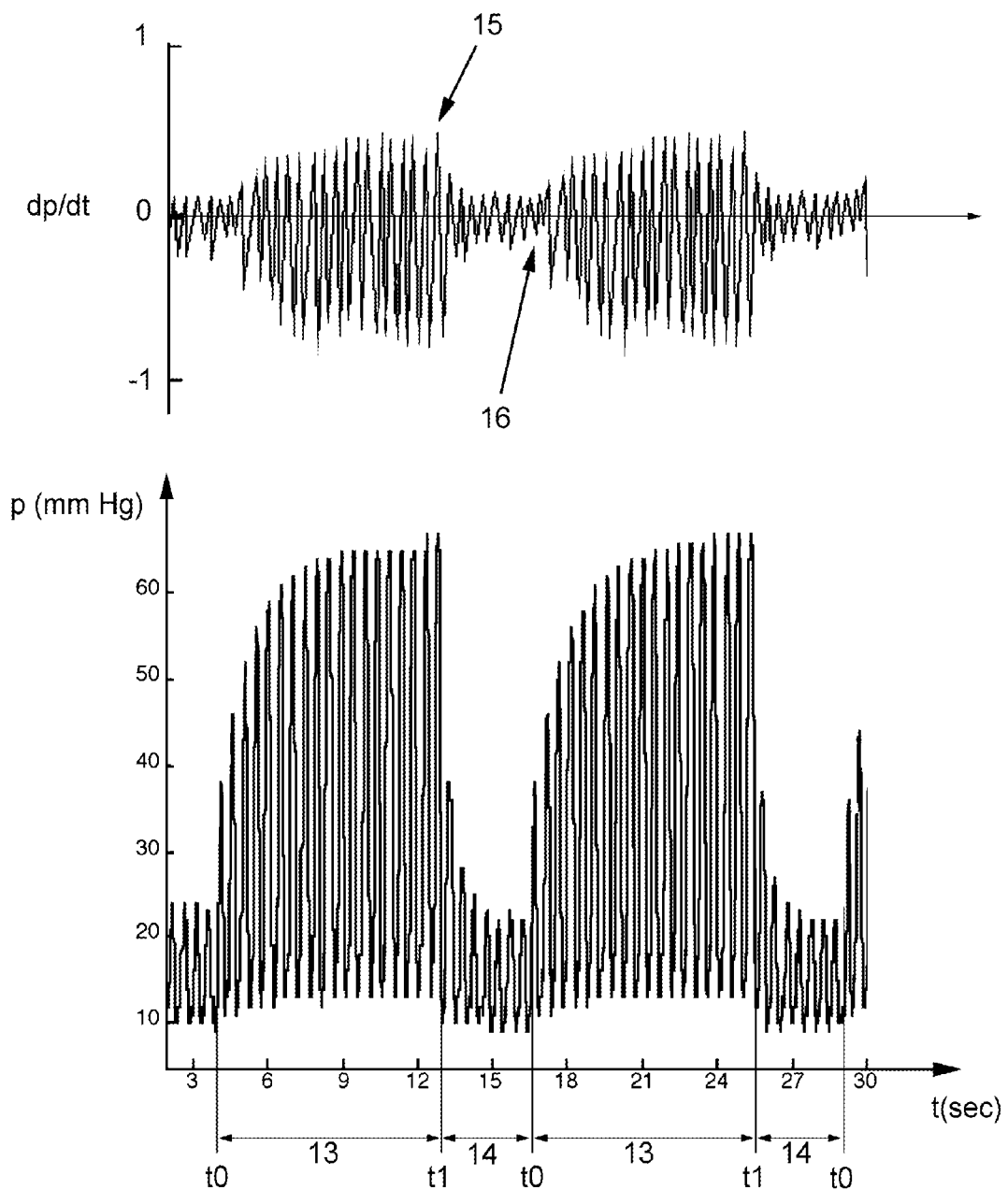
FIG. 3 compares the pressure curve and the derivative of the pressure curve with respect to time.
Figure 4:
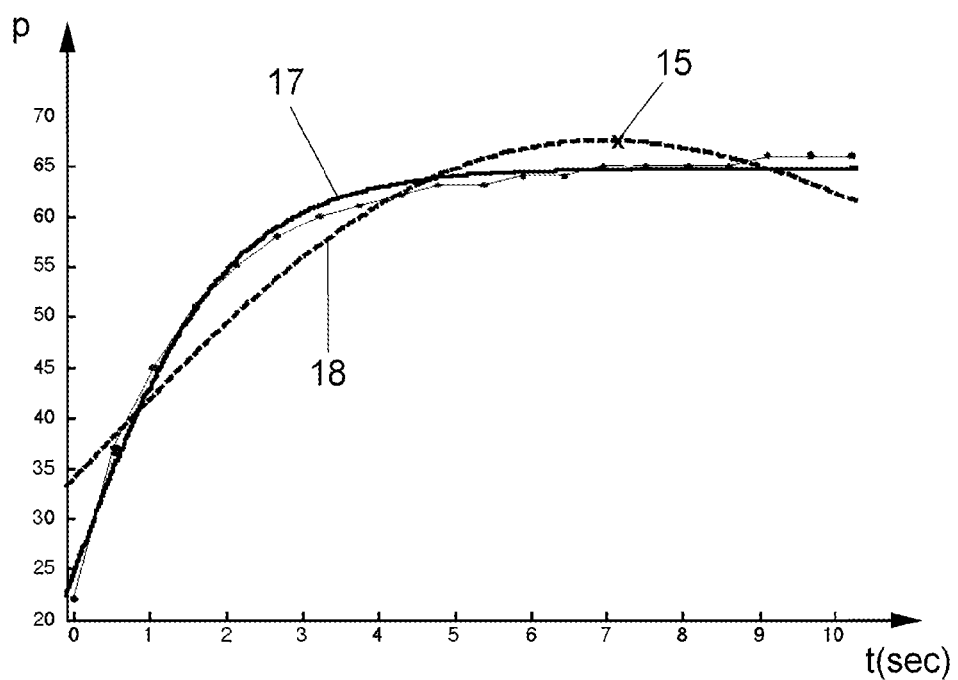
FIG. 4 illustrates the envelopes of the pressure curves according to FIG. 3.

FIG. 2*a* illustrates the pressure curve determined by the measuring device 7, with the beginning of the occlusion being shown at T0 and the end of the occlusion being shown at T1. A number of systolic pressure peaks 20 and a number of diastolic valleys 11 are to be seen. The pulse period 12 of the heart beat is represented by the time between consecutive peaks or consecutive valleys. During each heart beat within the occlusion phase 13, the speed of the pressure increase is determined by the calculation of the ratio $\Delta p/\Delta t$ as is schematically illustrated in the enlarged illustration of FIG. 2*b*. Something analogous occurs in the release phase 14 with the speed of the pressure decrease. For a time interval $\Delta t$ striving to zero, the calculation of a limit value results in an illustration according to FIG. 3, in which the pressure curve is compared to the respective curve of the first derivative $dp/dt$ of the pressure curve. It is apparent that the first derivative reaches a maximum in those points where the slope of the pressure curve is the largest within each heart beat. Similarly, it is apparent that the first derivative reaches a minimum in those points where the negative slope of the pressure curve is the smallest within each heart beat. Since, in the following, only the respective pressure maxima or pressure minima, respectively, occurring within a heart beat as well as the maxima and minima, respectively, of the first derivative of the pressure curve to be observed within each heart beat are of relevance, only the respective envelope curves connecting the respective maxima are illustrated in FIG. 4 for the sake of clarity. FIG. 4, thus, merely exemplifies the envelope curve for the phase of occlusion.

During the occlusion of the coronary sinus it is to be observed that the speed of the pressure increase rises continuously at consecutive heart beats, as is apparent from the envelope curve 17 of the first derivative. The optimum time for a release of the occlusion is in that point 15 in which the envelope curve 17 reaches its maximum, i.e., in which the speed of the pressure increase of consecutive heart beats is the highest. This time can be mathematically determined in the simplest way by equaling the second derivative of the pressure curve to zero. Hence results that a maximum is reached in point 15 of the envelope curve 17 of the first derivative of the pressure curve, whereas the envelope curve 18 connecting the systolic pressure peaks has already previously reached a plateau value. In an analogous manner, the optimum time for the triggering of the occlusion results to be in point 16 (FIG. 3).

By releasing the occlusion in point 15, it is, on the one hand, ensured that the occlusion will be maintained as long as possible such that a pressure level promoting the release of VEGF genes will prevail in the occluded coronary sinus as long as possible. On the other hand, harmful side-effects by too long an occlusion will be avoided, since the occlusion is released in time, namely as soon as the heart's contractibility declines.

To sum up, the present invention provides a method that is simple to perform and a device that is based on an algorithms simple to realize, thus rendering feasible the optimum and precise determination of both occlusion times and release times.

The invention claimed is:

1. A system for the intermittently occluding a coronary sinus in a heart, comprising:
   a multi-lumen catheter having an occlusion device along a distal end configured to be inserted into a coronary sinus of a heart via an atrium, wherein the occlusion device along the distal end of the multi-lumen catheter is intermittently adjustable to substantially occlude the coronary sinus of the heart;
   a pressure measuring device connected to the multi-lumen catheter, the pressure measuring device being configured to measure a fluid pressure in the occluded coronary sinus when the occlusion device occludes of the coronary sinus, and the pressure measuring device being in communication with a memory that stores data indicative of a fluid pressure curve as a function of time based upon the measured fluid pressure in the occluded coronary sinus when the occlusion device occludes the coronary sinus; and
   control circuitry configured to cause a release of the occlusion of the coronary sinus, wherein the control circuitry is configured to determine a pressure increase and/or pressure decrease per time unit while the coronary sinus is occluded by the occlusion device and configured to cooperate with the occlusion device to release the occlusion of the coronary sinus based at least in part on the pressure increase and/or pressure decrease per time unit.

2. The system of claim 1, wherein the control circuitry is configured to determine the pressure increase per time unit occurring at consecutive heart beats and to cooperate with the occlusion device to release the occlusion of the coronary sinus based at least in part on the pressure increase per time unit occurring at consecutive heart beats.

3. The system of claim 1, wherein the control circuitry is configured to determine a first derivative of the fluid pressure curve based upon the data stored in the memory that is indicative of the fluid pressure curve as the function of time.

4. The system of claim 3, wherein the control circuitry is configured to determine the first derivative of the fluid pressure curve with respect to time as well as a local maximum of the first derivative occurring within a heart beat, and the control circuitry being configured to cooperate with the occlusion device in a manner that the occlusion of the coronary sinus is released after the local maxima of consecutive heart beats have reached a maximum.

5. The system of claim 1, wherein the control circuitry is configured to trigger a start of a new occlusion of the coronary sinus using the occlusion device along the distal end of the multi-lumen catheter, wherein the control circuitry is configured to determine the pressure decrease per time unit and to cooperate with the occlusion device in a manner that the occlusion of the coronary sinus is triggered after the pressure decrease per time unit has reached a threshold.

6. The system of claim 5, wherein the control circuitry is configured to determine a first derivative of the fluid pressure curve with respect to time as well as a local minimum of the first derivative occurring within a heart beat, and the control circuitry being configured to cooperate with the occlusion device in a manner that the occlusion of the coronary sinus is triggered after the local minima of consecutive heart beats have reached a minimum.

7. The system of claim 1, wherein the multi-lumen catheter comprises a balloon inflation lumen that is connectable to a pump.

8. The system of claim 7, wherein the control circuitry is configured to deliver control signals to the pump so as to start and stop the pump when connected to the balloon inflation lumen.

9. The system of claim 1, wherein the pressure measuring device measures systolic pressure peaks occurring at consecutive heart beats while the coronary sinus is occluded.

10. The system of claim 9, wherein the pressure measuring device measures diastolic pressure valleys in the coronary sinus occurring between the systolic pressure peaks.

* * * * *